US012558052B2

(12) United States Patent
Palmer et al.

(10) Patent No.: US 12,558,052 B2
(45) Date of Patent: Feb. 24, 2026

(54) METHOD FOR MONITORING PET READOUT POSITIONS USING MRI FIDUCIALS

(71) Applicant: Sino Canada Health Institute Inc., Winnipeg (CA)

(72) Inventors: Vanessa Palmer, Winnipeg (CA); John Saunders, Winnipeg (CA); Ryan Sparkes, Winnipeg (CA); James Schellenberg, Winnipeg (CA); Graham Schellenberg, Winnipeg (CA)

(73) Assignee: Sino Canada Health Institute Inc., Hefei (CN)

( * ) Notice: Subject to any disclaimer, the term of this patent is extended or adjusted under 35 U.S.C. 154(b) by 1 day.

(21) Appl. No.: 17/428,446

(22) PCT Filed: Nov. 26, 2020

(86) PCT No.: PCT/CA2020/051614
§ 371 (c)(1),
(2) Date: Aug. 4, 2021

(87) PCT Pub. No.: WO2021/113957
PCT Pub. Date: Jun. 17, 2021

(65) Prior Publication Data
US 2022/0296196 A1     Sep. 22, 2022

Related U.S. Application Data

(60) Provisional application No. 62/945,468, filed on Dec. 9, 2019.

(51) Int. Cl.
*A61B 6/00*     (2024.01)
*A61B 6/03*     (2006.01)
(Continued)

(52) U.S. Cl.
CPC ............ *A61B 6/5247* (2013.01); *A61B 6/037* (2013.01); *A61B 6/107* (2013.01); *A61B 6/4417* (2013.01);
(Continued)

(58) Field of Classification Search
CPC ..................................................... A61B 6/5247
See application file for complete search history.

(56) References Cited

U.S. PATENT DOCUMENTS

| | | | |
|---|---|---|---|
| 9,200,017 | B2 | 12/2015 | Caravan |
| 9,606,245 | B1 | 3/2017 | Czarnecki et al. |
| 10,634,747 | B2 | 4/2020 | Majewski et al. |

OTHER PUBLICATIONS

Mackewn J E et al: "A fiducial marker based technique for alignment of simultaneously acquired PET and MRI images", 2009 IEEE Nuclear Science Symposium and Medical Imaging Conference (NSS/MIC 2009), Orlando, FL, USA, IEEE, Piscataway, NJ, USA, Oct. 24, 2009, pp. 3307-3310.
(Continued)

*Primary Examiner* — Joseph M Santos Rodriguez
(74) *Attorney, Agent, or Firm* — Michael R Williams; Ryan W Dupis; Ade & Company, Inc.

(57) ABSTRACT

Described herein is a method to measure the position of the PET System using the MRI, through the use of MRI coils and fiducials. This approach offers a route to automated calibration which is more flexible than other approaches. This method of position measurement is useful for example in systems which have moving or removeable PET readout board systems or moving or removeable PET scintillator blocks.

8 Claims, 4 Drawing Sheets

(51) Int. Cl.
   _A61B 6/10_          (2006.01)
   _A61B 6/50_          (2024.01)
   _A61B 90/00_         (2016.01)

(52) U.S. Cl.
   CPC ................ _A61B 6/501_ (2013.01); _A61B 6/54_
                (2013.01); _A61B 90/39_ (2016.02); _A61B_
                                    _2090/3954_ (2016.02)

(56)                References Cited

OTHER PUBLICATIONS

Marsden P k et al: "Simultaneous PET and NMR", British Journal of Radiology, London, GB, vol. 75, Jan. 2002, pp. S53-S59.

METHOD FOR MONITORING PET READOUT POSITIONS USING MRI FIDUCIALS

PRIOR APPLICATION INFORMATION

The instant application is a 371 of PCT Application CA2020/051614, now abandoned, which claimed the benefit of U.S. Provisional Patent Application Ser. No. 62/945,468, filed Dec. 9, 2019, now abandoned, and entitled "Method for Monitoring PET Readout Positions using MRI Fiducials", the entire contents of which are incorporated herein by reference for all purposes.

BACKGROUND OF THE INVENTION

Simultaneous PET and MRI systems can be designed as systems that are manufactured together into a single unit, or systems in which the PET is inserted into the MRI at the customer site and never removed again, or as systems in which the PET is inserted into and removed from the MRI at the customer site, with the insertion and removal being possible every day or week. For all of these systems, calibration and image registration are necessary to account for the performance differences that occur between the MRI and PET system. In particular, for combined simultaneous PET and MRI imaging systems in which the PET system is inserted and removed on a daily or weekly basis, it is useful to be able to have more flexible and automated calibration and image registration procedures. These flexible and auto- mated procedures can save customer time and expense and also lead to increased accuracy. One of the issues that occur with PET insert systems can be the exact locations of the scintillator blocks and readout boards of the PET system. This is because for PET Insert systems, the PET can be removed and replaced at the customer site, which means that a particular alignment may not be equivalent to the align- ment at the time of manufacture. The exact location of these readout boards must be known and maintained in order to achieve accurate reconstruction.

One method of achieving accurate positioning is through the manufacturing process, in which the tolerance of parts is maintained so that the tolerance required of the scintillator and readout system is achieved. This approach requires increased cost for the manufactured parts and may also be less useful if there are changes in the part locations due to servicing or other factors such as heating or cooling of the parts.

Prior Art PET imaging systems have been designed which use fiducials for identifying the location of objects.

For example, U.S. Pat. No. 5,947,981 identifies a fiducial method for head and neck therapy. There are a number of other patents and patent applications that reference this patent, all of which appear to use the fiducial approach within surgical or diagnostic imaging designs, but none of these use fiducials to measure PET readout element loca- tions.

Specifically, this patent teaches attaching graphic refer- ence means to a horizontal arm. The graphic reference means may comprise horizontal bars and a diagonal element which provide graphic reference indicia for image scanning. This enables referencing of the scan image data and the patient's anatomy relative to the horizontal arm.

There are also patents which use moving elements in PET systems to achieve various resolution and performance means, including: Movable integrated scanner for surgical imaging applications, U.S. Pat. No. 8,295,905, filed in 2007;

"Apparatus for Improving Image Resolution and Appa- ratus for Super-Resolution Photography Using Wobble Motion and Point Spread Function (PSF), in Positron Emis- sion Tomography", filed as an application US20110268334A1, in which the PET cylinder wobbles;

"Method for acquiring pet image with ultra-high resolu- tion using movement of pet device", which is an application, WO2013162172A1;

"Tomographic pet camera with adjustable diameter detec- tor ring" U.S. Pat. No. 5,825,031A granted in 1996, in which the diameter of the PET cylinder could be changed; and "Pet camera with individually rotatable detector modules and/or individually movable shielding sections", U.S. Pat. No. 6,744,053.

None of these PET related patents use fiducials for localization of the PET elements.

Rather, these system designs allowed the detector ele- ments to be moved in the radial direction to accommodate for object size, in the axial direction before imaging is started in order to customize for a surgical procedure, and in a wobbling motion to optimize sampling of the lines of response.

As will be appreciated by one of skill in the art, these types of removeable insert systems would benefit from a method to measure the location of the PET elements using MRI methods.

SUMMARY OF THE INVENTION

According to a first aspect of the invention, there is provided a PET ring comprising at least one PET readout element labelled with at least one MRI-detectable fiducial.

According to another aspect of the invention, there is provided, in an MRI system comprising an MRI bore:

a PET ring inserted into the MRI bore, said PET ring comprising at least one PET readout element labelled with at least one MRI-detectable fiducial.

According to another aspect of the invention, there is provided a BrainPET comprising:

a PET ring comprising at least one PET readout element labelled with at least one MRI-detectable fiducial an MRI coil inside the PET Ring, and an RF shield outside of the PET ring.

According to yet another aspect of the invention, there is provided a method of co-registering an MRI image and a PET image comprising providing a BrainPET comprising:

a PET ring comprising at least one PET readout ele- ment labelled with at least one MRI-detectable fidu- cial an MRI coil inside the PET Ring;

an RF shield outside of the PET ring; and a control unit comprising data acquisition, reconstruc- tion and analysis software;

said MRI coil detecting and locating the at least one MRI-detectable fiducial on the at least one PET readout element;

generating a PET scan of a patient using the PET ring;

generating an MRI scan of the patient using the MRI coil;

said data acquisition, reconstruction and analysis software determining the location of the at least one PET readout element relative to the MRI coil from the location of the MRI-detectable fiducial; and said data acquisition, reconstruction and analysis software co-registering the MRI scan and the PET scan from the location of the at least one PET readout element relative to the MRI coil.

According to a still further aspect of the invention, there is provided a method of co-registering an MRI image and a PET image comprising providing: an MRI system comprising an MRI bore; a work station comprising data acquisition, reconstruction and analysis software; and a BrainPET inserted into the MRI bore, said BrainPET comprising:

a PET ring comprising at least one PET readout element labelled with at least one MRI-detectable fiducial an MRI coil inside the PET Ring; and an RF shield outside of the PET ring;

said MRI coil detecting and locating the at least one MRI-detectable fiducial on the at least one PET readout element;

generating a PET scan of a patient using the PET ring;

generating an MRI scan of the patient using the MRI coil;

said data acquisition, reconstruction and analysis software determining the location of the at least one PET readout element relative to the MRI coil from the location of the MRI-detectable fiducial; and said data acquisition, reconstruction and analysis software co-registering the MRI scan and the PET scan from the location of the at least one PET readout element relative to the MRI coil.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is a method for co-registering MRI and PET scans by measuring the position of the readout elements of the PET System using the MRI, through the use of MRI coils and MRI-detectable fiducials. This approach offers a route to automated calibration which is more flexible than other approaches. This method of position measurement is useful for example in systems which have moving or removeable PET readout board systems or moving or removeable PET scintillator blocks.

As will be appreciated by one of skill in the art, such an arrangement can be used for co-registration of MRI and PET scans in any MRI/PET imaging system. As discussed herein, the method is ideal for co-registration of simultaneous MRI and PET images but may of course be used to co-register non-simultaneous images as well.

Figure 1:
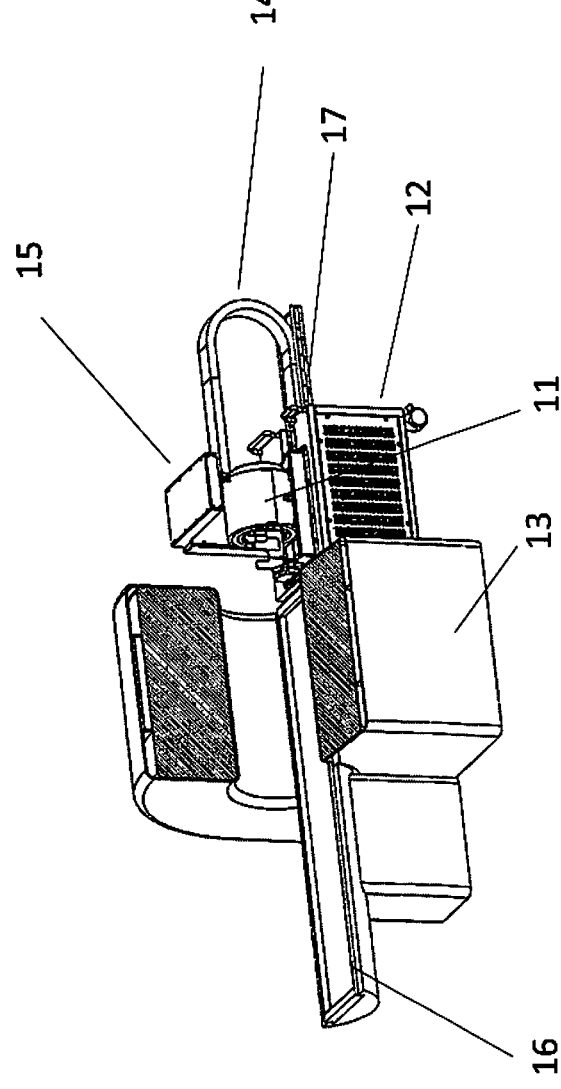
FIG. 1 shows an MRI, a cart, and a BrainPET scanner.

For example, assuming a system that comprises a Brain-PET Imaging system which is arranged to be inserted into an MRI system, the MRI system including at least:

a previously installed MRI, a docking station, a BrainPET Insert that slides or is placed into the MRI, and a workstation installed in the MRI control room with appropriate data acquisition, reconstruction and analysis software;

Parts of such a system are shown in FIG. 1. Specifically, FIG. 1 is a drawing of the the the BrainPET system showing the BrainPET scanner 11 and cart 12 at the back of the MRI 13. The BrainPET scanner 11 is connected to the cart 12 by a copper cable 14 and cable management system 17. In some embodiments, this copper cable 14 has a length of 10 to 20 feet depending on the type of MRI that is being used. The scanner weighs between 50 and 100 pounds, and so a scanner movement system 15 is required to lift the scanner and place it on the MRI patient bed 16. This figure shows a cart, MRI, insert and cable management method. The Brain-PET workstation and fiber connection to the workstation are not shown.

In one embodiment, the BrainPET scanner comprises:

an MRI coil inside the PET Ring, and a PET ring with readout elements, for example scintillator and detector elements, including at least one MRI detectable fiducial placed on at least one of the readout elements.

Figure 2:
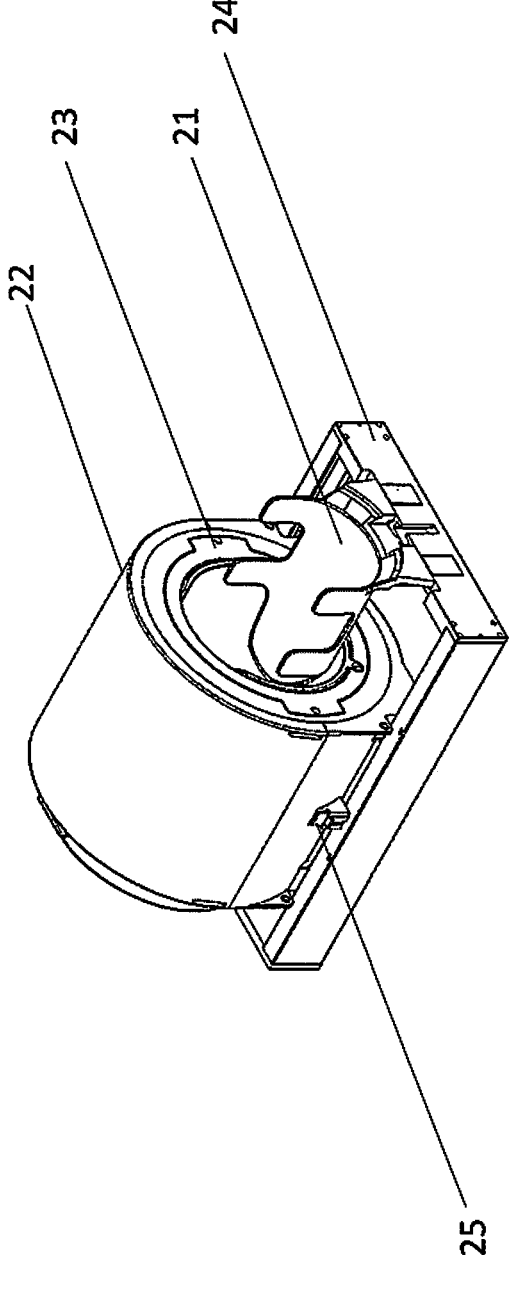
FIG. 2 shows the parts of the PET Scanner, comprising a headholder, Rx Coil, Tx coil and PET Ring.

FIG. 2 shows one embodiment of the BrainPET scanner showing Head Holder 21, PET Ring 22, Tx and Rx coil 23. The PET Ring 22 and TX and Rx coil 23 are connected together into a single moveable unit, and they slide forwards and back on the Slide Platform 24. There are two locking positions for the PET Ring 22 and Tx and Rx coil 23, with the back or front position both being locked in place using the locks 25 on the side of the PET Ring 22. Only one lock 25 is shown in this view. The Rx coil is at the inner-most position within the insert; the Tx coil is outside of and adjacent to the Rx coil and both the Rx coil and the Tx coil are within the PET ring 22. In some embodiments, approximate dimensions of the Scanner are a 26.5 cm diameter inner bore, an Rx coil that extends from 26.5 cm to 28 cm, a Tx coil that extends from 28 cm to 32 cm, and a PET ring that extends from 32 cm to 44 cm diameter. As will be appreciated by one of skill in the art, these dimensions can be different for different specific designs and different versions of MRI.

The BrainPET scanner or PET Insert comprises a headholder, an Rx Coil, a Tx coil and a PET Ring. In this embodiment the Headholder, Rx Coil and Tx Coil are removable from the PET ring for calibration purposes. In this embodiment, a slide section is also shown which allows the scanner to be moved to forward and back locations and locked in place. Not all embodiments require the slide capability.

However, when the coils are replaced and/or reinserted, it is important to measure their position to ensure that the calibration tables that are used are the correct ones, or as an indication that the alignment of the elements are not correct, or as an indication that new calibration tables need to be installed.

Figure 3:
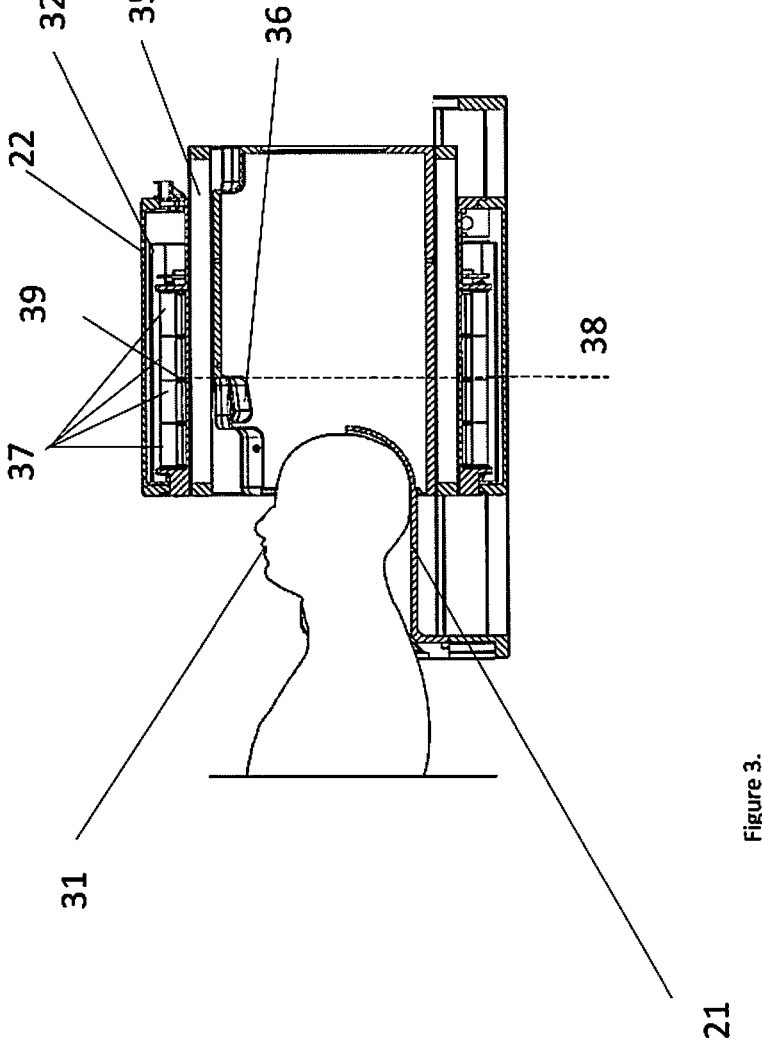
FIG. 3 shows a cross sectional view of the PET ring with the coil in place.

FIG. 3 shows a side view schematic drawing showing the patient's head 31 positioned on the headholder 21 and the PET Ring 22, inside of which is the Tx coil 35, inside of which is the Rx coil 36. Inside the PET ring 22 are positioned the 4 scintillator blocks 37. The axial positioning of these scintillator blocks identify or establish the PET Center of the field of view 38. In this example, one MRI fiducial 39 is shown positioned between scintillator blocks 2 and 3. As will be appreciated by one of skill in the art, in some embodiments, multiple fiducials may be placed on the scintillator and readout boards.

Figure 4:
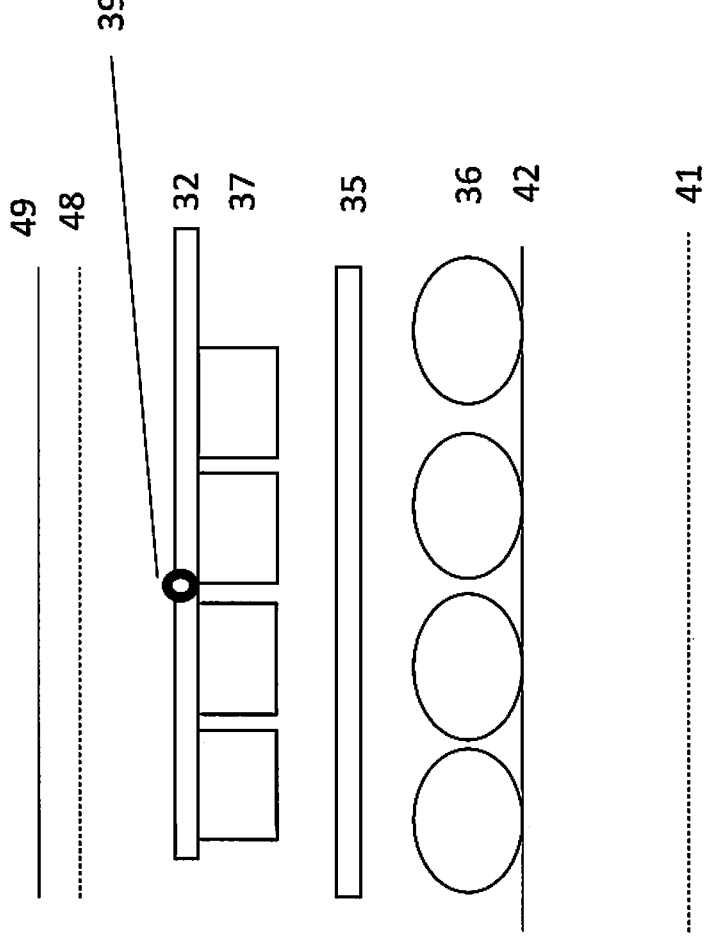
FIG. 4 is a schematic diagram of the BrainPET scanner elements.

FIG. 4 shows a "closer" view of the scanner elements, moving from middle of the bore to outer edge. As can be seen, this comprises in order with increasing distance from the center of field of view 41, the inner plastic bore of the scanner assembly 42, the Rx receive coil elements 36 which in this case is shown as 4 circles indicating Rx loops; the transmit element 35 which are shown as a single transmit line, but in reality there may be multiple transmit lines organized symmetrically around the circumference; the readout board 32 and four scintillator blocks 37 with a fiducial 39 located on the board; an RF shield 48 and the outside cover of the scanner 49. In one embodiment, the radius of these elements from the middle of the bore can be designed to be 13.25 cm from the middle of the bore to the inner plastic bore of the scanner assembly, 14 cm to the start of the Tx assembly, 16 cm to the bottom of the scintillators, and 22 cm to the outer cover of the scanner 49. The scintillators are typically 2 cm thick, and the readout boards can be less than 1 cm thick. This allows extra space between readout board and outer cover for appropriate heat dissipation and cabling room. The scintillators are typically blocks in the approximate axial dimensions of 49 mm, with a typical gap of between 1 and 2 mm between the blocks. This gap allows for ease of manufacturing, and the gap can be stuffed with material to ensure that the scintillator blocks do not touch one another during manufacturing and operation.

The Readout Boards consist of SiPM pixels that convert light into electrical signals, and readout board resistors and capacitors, optical glue or gel, and reflective tapes and optical methods to allow readout or detection of the scintillation events. On this readout board can be placed MRI detectable fiducials.

MRI-detectable fiducials are generally and have previously been used on patients during imaging, and are used for identifying "landmarks" during imaging, for example, anatomical sites or regions on the patient. Suitable MRI-detectable fiducial materials include but are by no means limited to copper sulfate, iodine and gold particles. Other suitable materials for MRI-detectable fiducials for use within the invention will be readily apparent to one of skill in the art.

The fiducials can be purchased from vendors specialized in their design. Typically, they are gel or liquid inside a capsule, and approximately round in shape.

As will be appreciated by one of skill in the art, because of manufacturing tolerances, the readout board cannot be more than 2 mm out of position. That is, any defective readout board would be identified during the manufacturing process and/or during the manufacturing acceptance process. Specifically, the board and assembly would never be shipped if such a large misplacement occurred. However, even a misplacement of less than 2 mm is significant when aligning or co-registering MR and PET images. However, the combination of the fiducials and imaging software arranged for fiducial localization software allows for automated alignment of the images. As discussed herein, the combination of fiducials and software designed to detect the fiducials and align the scans based on the location of the fiducials and therefore the location of the PET readout elements will adjust for a fiducial that is 1 or 2 mm out of alignment. In some embodiments, more than one fiducial may be placed on the respective readout element, preferably in an asymmetrical pattern for alignment purposes, leading to in aggregate a more accurate alignment.

The location of the fiducial is controlled mechanically by the design of the board and is typically within 1 mm of the desired location. Even with a fiducial that is placed within 1 mm of the desired location, when one has many fiducials to average with, the resulting accuracy of the image alignment is better than 1 mm.

As discussed herein, outside of the readout board is an RF Shield that is part of the MRI coil system. Because the shield is outside of the readout board, the fiducial is in the field of view of the Rx coil. As a result of this arrangement, the MRI detectable fiducial is visible to the MRI system. The MRI system can automatically line up the fiducials, which are in a known location with respect to the readout board elements, with a known spatial orientation so that location of the fiducials, and hence the location of the readout boards and PET elements, are known.

For a typical BrainPET system, there will be 16 or more readout boards organized around the circumference of the PET Ring. In some embodiments, each of these readout boards may have at least one MRI-detectable fiducials. As will be apparent to one of skill in the art, having more than one MRI-detectable fiducial, for example, two or more MRI-detectable fiducials on a given PET readout element such as for example a readout board or a scintillation block provides increasing levels of accuracy regarding the positioning of the readout elements. In this manner, the location of each readout element, for example, each readout board and/or scintillation element, can be calibrated and/or adjusted if necessary or alternatively the co-registration of the images can be adjusted, as discussed herein.

In one aspect of the invention, there is provided a PET ring comprising at least one PET readout element labelled with at least one MRI-detectable fiducial.

As will be appreciated by one of skill in the art, such a PET ring can be placed within an MRI bore and used for co-registration of the PET and MRI scans or images using the method described herein.

As discussed herein, the at least one PET readout element is a readout board or a scintillation block.

As discussed herein, the at least one readout element may comprise two or more MRI-detectable fiducials arranged asymmetrically relative to each other. Specifically, using two or more MRI-detectable fiducials allows for more accurate co-registration.

In another aspect of the invention, there is provided an MRI system comprising an MRI bore; a PET ring inserted into the MRI bore, said PET ring comprising at least one PET readout element labelled with at least one MRI-detectable fiducial.

As will be appreciated by one of skill in the art, in these embodiments, the PET ring is inserted into an MRI bore. This insertion may be temporary (i.e. the PET ring is removable) or permanent (i.e. the MRI system either included a PET ring within the bore or has been retrofitted to include a PET ring).

In another aspect of the invention, it is possible that the MRI body coil can be used as the Tx coil, in which case only the PET ring and Rx coil are designed to be close to the patient head.

In some embodiments of the invention, there is provided a BrainPET comprising: a PET ring comprising at least one PET readout element labelled with at least one MRI-detectable fiducial, an MRI coil inside the PET Ring, and an RF shield outside of the PET ring.

While this arrangement is referred to as a "BrainPET", it is important to note that such a device may be used for simultaneous MRI and PET scanning of body parts other than the brain, as will be apparent to one of skill in the art.

It is further noted that as used herein, "simultaneous" in regards PET and MRI scan generation does not necessarily mean that the scans are taken at the exact same instant in time, but may mean that the scans are taken within a sufficiently narrow window of time that they are taken without moving the patient or without movement by the patient.

According to another aspect of the invention, there is provided a method of co-registering an MRI image and a PET image comprising providing a BrainPET comprising:

a PET ring comprising at least one PET readout element labelled with at least one MRI-detectable fiducial an MRI coil inside the PET Ring;

an RF shield outside of the PET ring; and a control unit comprising data acquisition, reconstruction and analysis software, said MRI coil detecting and locating the at least one MRI-detectable fiducial on the at least one PET readout element;

generating a PET scan of a patient using the PET ring;

generating an MRI scan of the patient using the MRI coil;

said data acquisition, reconstruction and analysis software determining the location of the at least one PET readout element relative to the MRI coil from the location of the MRI-detectable fiducial; and said data acquisition, reconstruction and analysis software co-registering the MRI scan and the PET scan from the location of the at least one PET readout element relative to the MRI coil.

According to another aspect of the invention, there is provided a method of co-registering an MRI image and a PET image comprising providing: an MRI system comprising an MRI bore; a work station comprising data acquisition, reconstruction and analysis software; and a BrainPET inserted into the MRI bore, said BrainPET comprising:

a PET ring comprising at least one PET readout element labelled with at least one MRI-detectable fiducial an MRI coil inside the PET Ring; and an RF shield outside of the PET ring;

said MRI coil detecting and locating the at least one MRI-detectable fiducial on the at least one PET readout element;

generating a PET scan of a patient using the PET ring;

generating an MRI scan of the patient using the MRI coil;

said data acquisition, reconstruction and analysis software determining the location of the at least one PET readout element relative to the MRI coil from the location of the MRI-detectable fiducial; and said data acquisition, reconstruction and analysis software co-registering the MRI scan and the PET scan from the location of the at least one PET readout element relative to the MRI coil.

As will be apparent to one of skill in the art, the MRI coil carries out two separate and distinct functions.

Specifically, the MRI coil scan the patient in a first plane or direction, that is, below the MRI coil, but also detects the MRI-detectable fiducials on the PET readout elements in a second plane of direction, that is, above the MRI coil.

That is, in use, the receive coil of the MRI coil receives images from the entire volume inside the RF shield. Therefore, by placing the shield outside of the PET readout boards, the PET readout boards are now in the field of view of the MRI coil. Thus, by putting MR fiduciary on the readout boards, the fiducials are visible also even though the images that the MRI technician would see, that is, the images that would be presented by the imaging software would only be the MRI scan of the patient. Thus, while the technician would not necessarily see the fiducials, the MRI system, that is, the control unit or work station, "sees" the entire image or entire volume within the RF shield. As discussed above, once the MRI system or control unit or work station sees all of the MRI-detectable fiducials, the PET and MRI images are aligned based on the relative locations of the MRI coil and the MRI-detectable fiducial-labeled PET readout elements.

It is of note that the detection of the MRI-detectable fiducials by the RF coil may be done prior to the scans of the patient, for example, prior to the patient entering the scanning area or device, or may be carried out at generally the same time as the PET scan and MRI scan, as discussed herein.

While the preferred embodiments of the invention have been described above, it will be recognized and understood that various modifications may be made therein, and the appended claims are intended to cover all such modifications which may fall within the spirit and scope of the invention.

The invention claimed is:

1. A method of co-registering an MRI image and a PET image comprising providing a BrainPET comprising:

a PET ring comprising at least one PET readout element labelled with at least one MRI-detectable fiducial an MRI coil inside the PET Ring;

an RF shield outside of the PET ring; and a control unit comprising data acquisition, reconstruction and analysis software said MRI coil detecting and locating the at least one MRI-detectable fiducial on the at least one PET readout element;

generating a PET scan of a patient using the PET ring;

generating an MRI scan of the patient using the MRI coil;

said data acquisition, reconstruction and analysis software determining the location of the at least one PET readout element relative to the MRI coil from the location of the MRI-detectable fiducial; and said data acquisition, reconstruction and analysis software co-registering the MRI scan and the PET scan from the location of the at least one PET readout element relative to the MRI coil.

2. The method according to claim 1 wherein the at least one PET readout element is a readout board or scintillation block.

3. The method according to claim 1 wherein the at least one readout element comprises two or more MRI-detectable fiducials arranged asymmetrically relative to each other.

4. The method according to claim 1 wherein the PET scan and the MRI scan are performed simultaneously.

5. A method of co-registering an MRI image and a PET image comprising providing: an MRI system comprising an MRI bore; a work station comprising data acquisition, reconstruction and analysis software; and a BrainPET inserted into the MRI bore, said BrainPET comprising:

a PET ring comprising at least one PET readout element labelled with at least one MRI-detectable fiducial an MRI coil inside the PET Ring; and an RF shield outside of the PET ring;

said MRI coil detecting and locating the at least one MRI-detectable fiducial on the at least one PET readout element;

generating a PET scan of a patient using the PET ring;

generating an MRI scan of the patient using the MRI coil; 5 said data acquisition, reconstruction and analysis software determining the location of the at least one PET readout element relative to the MRI coil from the location of the MRI-detectable fiducial; and said data acquisition, reconstruction and analysis software 10 co-registering the MRI scan and the PET scan from the location of the at least one PET readout element relative to the MRI coil.

6. The method according to claim 5 wherein the at least one PET readout element is a readout board or scintillation 15 block.

7. The method according to claim 5 wherein the at least one readout element comprises two or more MRI-detectable fiducials arranged asymmetrically relative to each other.

8. The method according to claim 5 wherein the PET scan 20 and the MRI scan are performed simultaneously.

* * * * *